United States Patent [19]
Sachse

[11] Patent Number: 5,074,849
[45] Date of Patent: Dec. 24, 1991

[54] URETER DRAINAGE TUBE WITH FIXABLE AUXILIARY TUBE

[76] Inventor: Hans-Ernst Sachse, Lerchenstr. 55, 8500 Nuernberg 90, Fed. Rep. of Germany

[21] Appl. No.: 468,017

[22] Filed: Jan. 22, 1990

[51] Int. Cl.⁵ ............................................. A61M 5/00
[52] U.S. Cl. ................................... 604/280; 604/264; 604/283
[58] Field of Search .......................... 604/280, 8-10, 604/57, 264, 281, 282, 283

[56] References Cited

U.S. PATENT DOCUMENTS 4,713,058 12/1987 Sachse ................................ 604/165
4,738,667 4/1988 Galloway ........................... 604/281
4,798,591 1/1989 Okada ................................ 604/281
4,820,262 4/1989 Finney ................................ 604/8

Primary Examiner—Max Hindenburg
Assistant Examiner—Ralph A. Lewis
Attorney, Agent, or Firm—Keil & Weinkauf

[57] ABSTRACT

A drainage tube (drainage split for the ureter) with mandrin and auxiliary tube, designed so that all three elements can be connected with each other by screwing in such a manner that, upon insertion into the body tubes, such as for example the ureter, they form functionally a unit of a stability such that the three elements, upon insertion, when slid in either direction, cannot be separated from each other.

11 Claims, 4 Drawing Sheets

URETER DRAINAGE TUBE WITH FIXABLE AUXILIARY TUBE

DESCRIPTION

FIELD AND BACKGROUND OF THE INVENTION

Drainage tubes, often simply called splint tubes and made of elastic material, have long been known in medicine and they serve to hold open narrowed body organs and facilitate the passage of body fluids or flushing fluids from one cavity into another, or to the outside. A very frequent area of application for such drainage tubes is the splinting of the ureter. In this splinting of the ureter urine is passed from the kidney pelvis into the bladder or the splinting also shunts the urethra and it conducts the urine from the kidney pelvis by way of the ureter, the bladder, and the urethra to the outside. For the securing of the drainage tube it has proved very helpful to prevent the sliding of the drainage tube out of the kidney pelvis, and insure its maintenance therein, by means of an inherent curvature of the tip of the drainage tube. For their introduction, these drainage tubes which because of their curved shape are known as "pigtail" splint tubes, must be brought into a straightened stretched form. The inherent curvature of the tip and of the end of the drainage tube is evened out by a relatively stiff mandrin. This mandrin has an additional task. It serves for the insertion of an auxiliary tube. As a rule, one end of the drainage tube lies in the kidney pelvis and the other end lies in the bladder. The placement of such a splint tube takes place with the aid of a cystoscope. The surgeon introduces the cystoscope through the urethra into the bladder, optically locates the outlet of the ureter and shoves the tip of the drainage tube through the ureter outlet into the ureter and subsequently slides the drainage tube upwardly and thus in the direction of the kidney until the tip of the drainage tube comes to lie in the kidney pelvis. For this introduction process into the ureter the drainage tube tip which because of its inherent curvature is bent around, must be straightened and this is effected by a stiff mandrin. In order to place the drainage tube (sleeve) 22 which is slightly longer than the ureter, in such a way that the curvature of the drainage tube in the range of the drainage tube tip lies in the kidney pelvis and the curvature in the range of the drainage tube end lies in the bladder, a second little tube, that is, an "auxiliary splint tube" is required. This auxiliary splint tube upon initial placement of the drainage tube over the mandrin is also slid onto the mandrin and it makes it possible to advance the drainage tube end through the cystoscope shaft into the bladder. The mandrin also avoids, for the introduction process, the inherent curvature of the drainage tube end, which curvature is to prevent that the end of the drainage tube pulls itself completely into the ureter.

OBJECT AND SUMMARY OF THE INVENTION

It is an object of the present invention to firmly connect the auxiliary tube with the drainage tube by means of a screw connection so that in the difficult introduction process pulling back as well as rotational movement of the drainage tube is made possible easily and without problems.

This screw connection between drainage tube and auxiliary tube takes place, according to the invention in that the mandrin (4) at its tip (1) has an external thread (2) opposite which there is provided in the interior lumen of the drainage tube, in the range of its tip a corresponding wall profile in the form of a counter thread (3) into which the exterior thread of the mandrin, upon corresponding rotational movement screws itself and upon rotational movement in the opposite sense unscrews again; or instead of the wall profile a small tube with an interior thread is provided.

A similar screw connection can be provided between drainage tube and mandrin also in the range of the drainage tube end. In this embodiment the mandrin in the range of its tip does not have screw threads but instead it has, in its center section, an external thread (11) opposite which there is provided a counter thread (12) in the interior lumen of the drainage tube end range, which can here be screwed in.

In order to facilitate easy and safe unscrewing drainage tube and auxiliary tube, at their surfaces of engagement have rectangular recesses and projections which act like a gear and prevent longitudinal displacement or rotational movement between drainage tube and auxiliary tube.

Preferably, the drainage tube and the auxiliary tube mesh by means of slanted recesses (14) and corresponding projections (15) at the drainage tube end and the auxiliary tube tip.

Undesired rotational movements of the mandrin within the drainage tube are prevented here by the fact that the angularly profiled mandrin tip reaches into a correspondingly profiled interior lumen of the tip range of the drainage tube. The auxiliary tube, additionally, is pressed onto the mandrin by means of a clamping ring (16) in the end range.

The insertion of the drainage tube occurs, in the following manner: First, the auxiliary tube is loosely connected up by means of the mandrin which latter is somewhat longer than the drainage tube and the auxiliary tube together. Following this, the mandrin with its external thread in the tip range is screwed into the counter thread in the interior lumen of the drainage tube tip. The tip of the auxiliary tube is advanced towards the end of the drainage tube until, the end of the drainage tube meshes with the tip of the auxiliary tube by virtue of their profiles. This mutual position between drainage tube, auxiliary tube and mandrin is now fixed by means of a clamping ring, provided on the auxiliary tube in the and range, or by means of a clamp attached at this location. The screw connection of drainage tube and auxiliary tube is effected in a similar manner. In this case the screw connecting by means of the mandrin does not take place in the tip range but in the end range of the drainage tube.

The securing of the drainage tube on the auxiliary tube may take place by means of a screw connecting facility realized through corresponding recesses and projections on the drainage tube end and the auxiliary tube tip. Here, prior to insertion into the body, the auxiliary tube is first placed onto the mandrin and subsequently the drainage tube is placed on top. The mandrin is now advanced into the drainage tube until its angularly profiled tip has fitted itself fully into the correspondingly formed interior lumen section of the drainage tube tip. Subsequently drainage tube end and auxiliary tube tip are connected with each other by rotational movement and are pressed onto the mandrin by means of the clamping ring of the auxiliary tube end. This functional unit is inserted in the described manner. After the drainage tube tip has been properly placed in the kidney pelvis the clamping ring is released. While the angular profile of the mandrin tip holds the drainage tube in its position, the screw connection to the drainage tube can be released again by means of a rotational movement of the auxiliary tube and subsequently by virtue of the removal of the mandrin and the auxiliary tube, the drainage tube is left in the body.

BRIEF DESCRIPTION OF THE DRAWINGS

The subject of the invention is described hereinafter by means of embodiments illustrated in FIGS. 1, 2 and 3.

DETAILED DESCRIPTION OF EMBODIMENT

Figure 1:
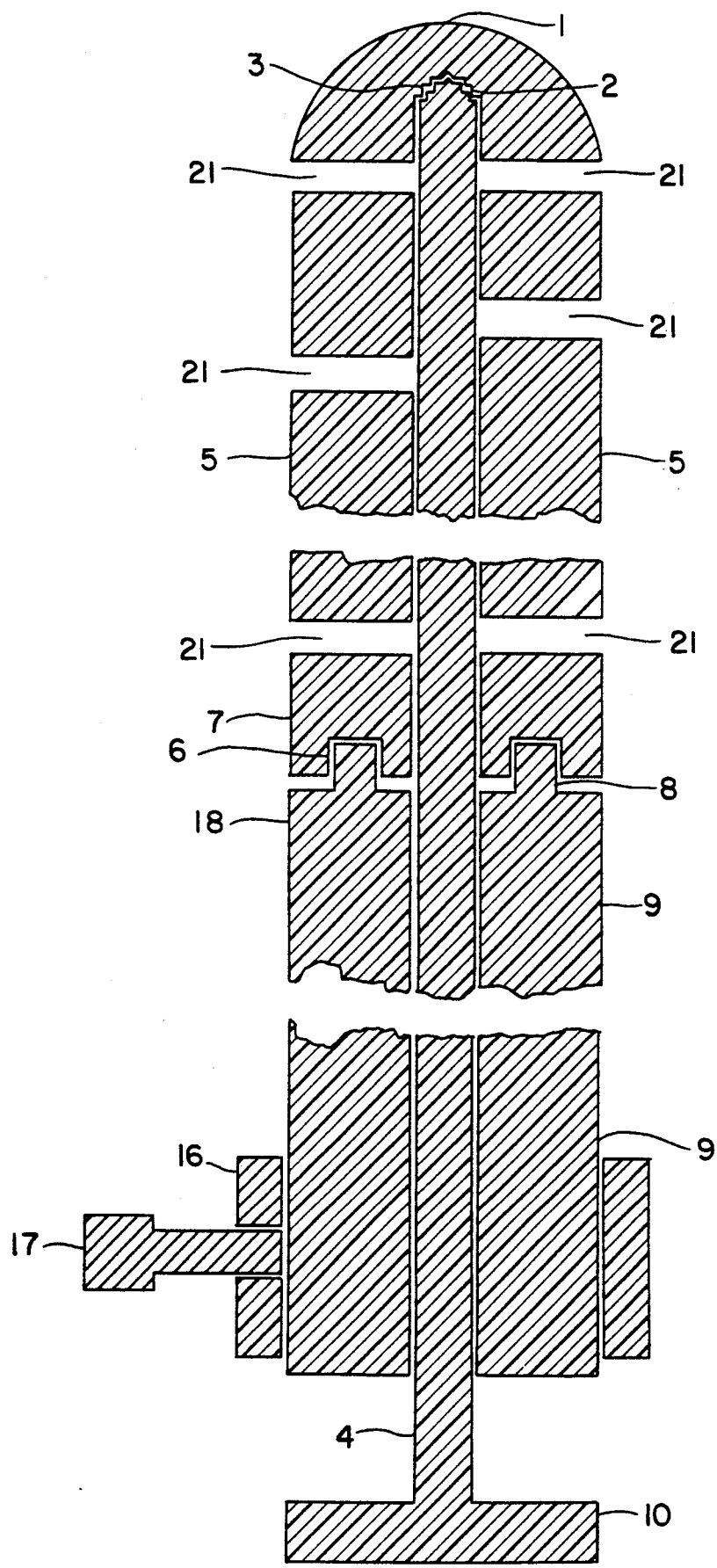
FIG. 1 shows a longitudinal section through the drainage tube with mandrin and auxiliary tube, with the screw connection in the tip range of the drainage tube.
Figure 4:
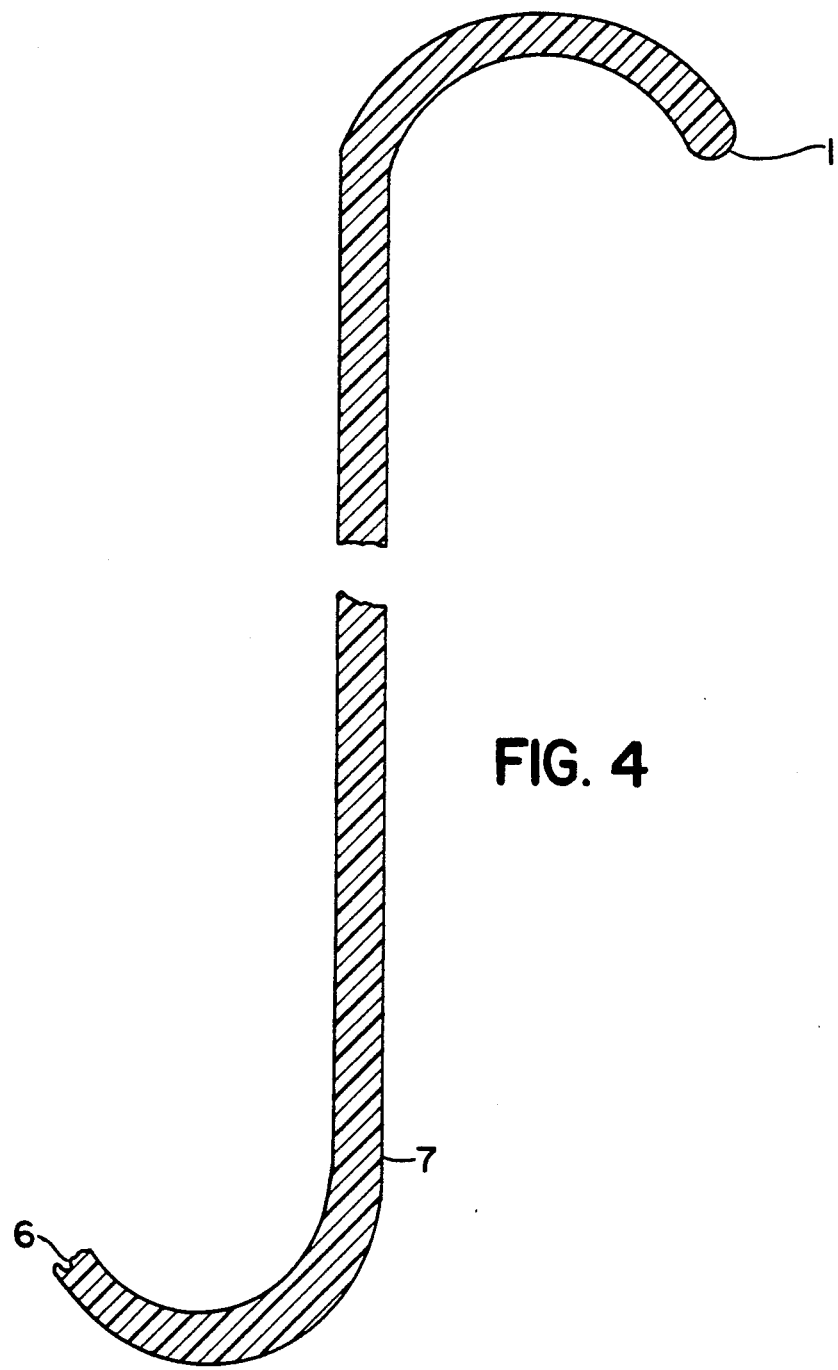
FIG. 4 is a schematic showing of the drainage tube, illustrating its original, non-straightened-out condition.

FIG. 1 shows a longitudinal section through the drainage tube (5), the mandrin (4) and the auxiliary tube (9). The screw-mandrin (4) consists of a hard elastic material and has in the range of its tip an external thread (2) which can be screwed into or out of the counter thread of the drainage tube (5). With this screwing in or screwing out the mandrin (4) is firmly connected with the drainage tube (5) or is again separated therefrom. These rotational movements are facilitated by means of the handpiece (10). The auxiliary tube (9) which is slid onto the mandrin (4) and which upon correct placement of the drainage tube can be removed again together with the mandrin, serves to facilitate the advancement of the drainage tube (5) through the ureter and the bladder. In order that the auxiliary tube (9), incident to the rotational movements of mandrin (4), cannot be rotationally displaced relatively to the drainage tube (5) the auxiliary tube (9) is provided with projections (8) which engage corresponding recesses (6) of the drainage tube (7) and which lead to a gearing of the auxiliary tube (9) with the drainage tube (5). A clamping ring 16 which can also be replaced by an, ordinary clamp, firmly presses the auxiliary tube onto the mandrin and it insures that the engagement cannot be prematurely released. FIG. 4 is a schematic showing of the drainage tube of FIG. 1, in its original, non-straightened-out condition.

Figure 2:
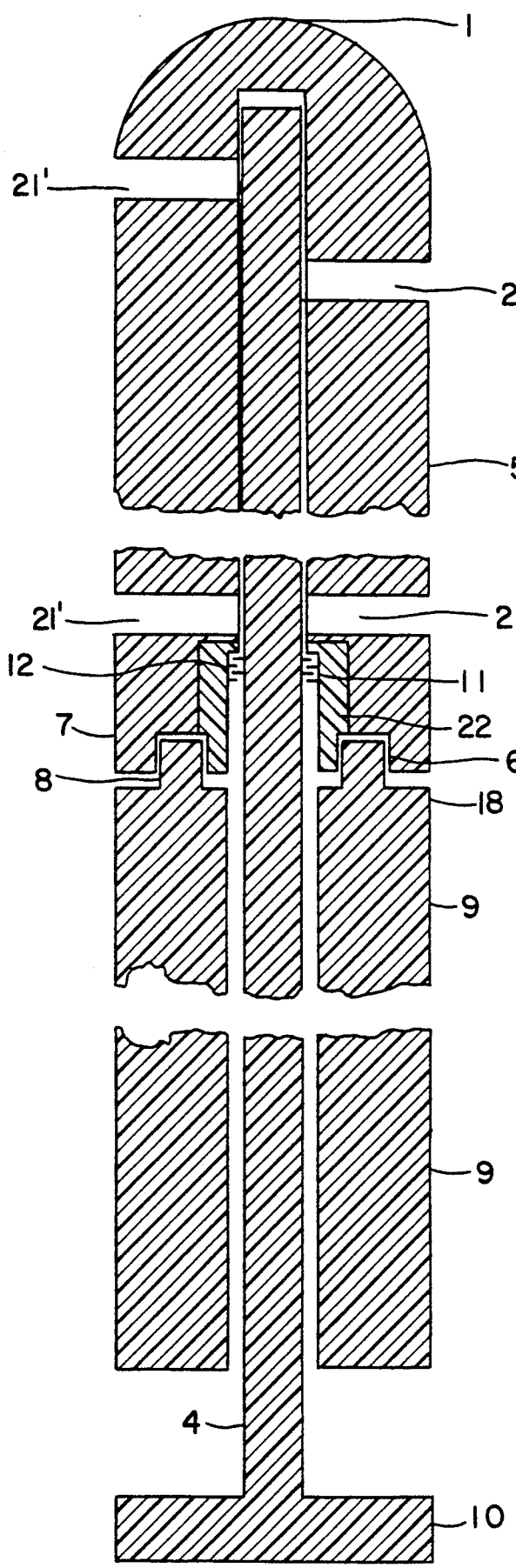
FIG. 2 shows a longitudinal section through the drainage tube with mandrin and auxiliary tube, with a screw connection in the end range of the drainage tube.

In FIG. 2 there is illustrated a longitudinal section through the drainage tube (5), the mandrin (4) and the auxiliary tube (9), with a screw connection in the range of the drainage tube end (7). In this embodiment the screw connection does not take place in the tip range but in the end range (7) of the drainage tube (1). The external thread (11) on the mandrin shaft (4) cooperates with a counter thread (12) in the range of the drainage tube end. All other elements correspond to FIG. 1.

Figure 3:
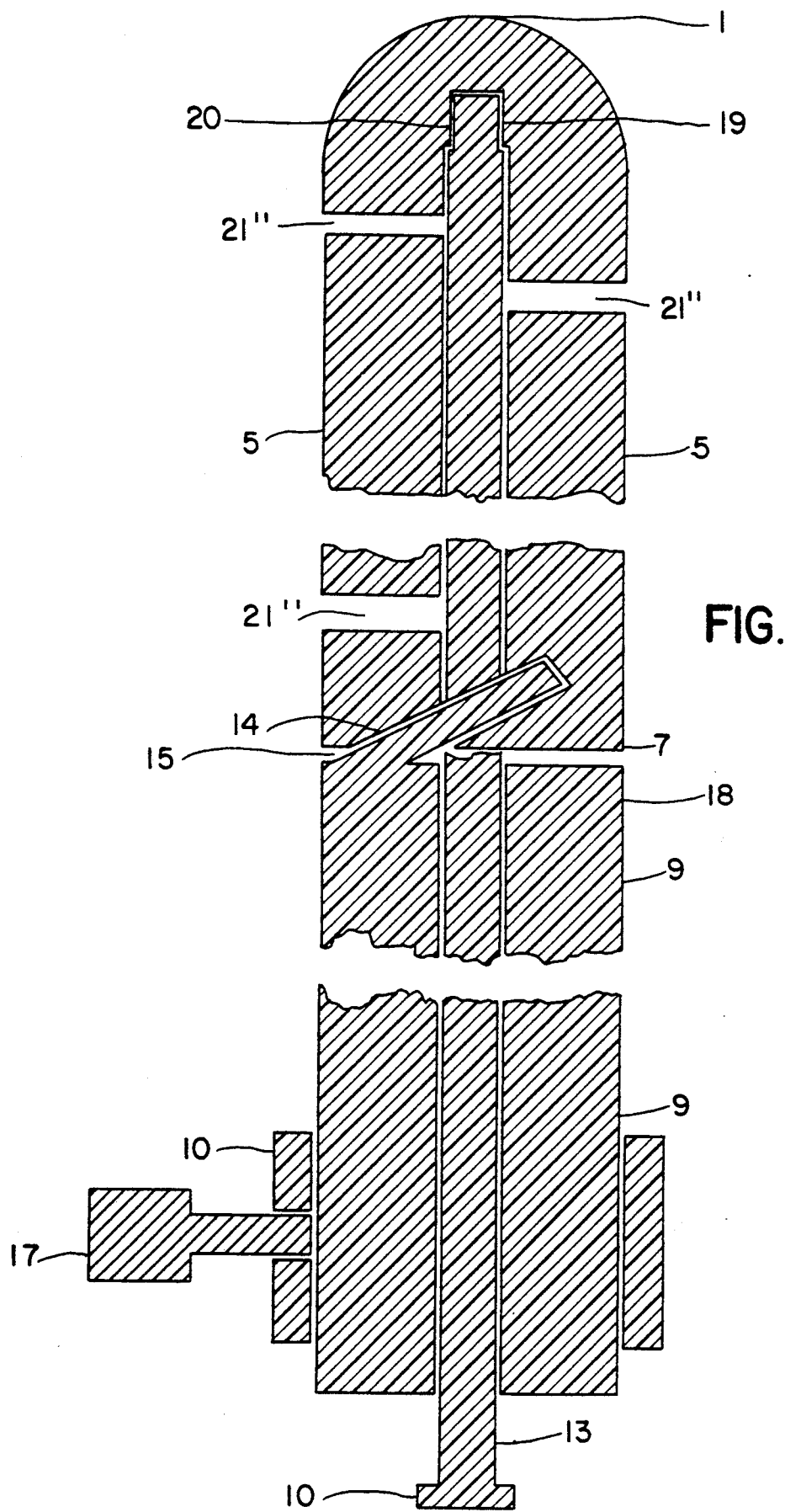
FIG. 3 shows a longitudinal section through the drainage tube with mandrin and auxiliary tube with a screw connection of the walls of drainage tube and auxiliary tube.

In FIG. 3 there is shown a longitudinal section through the drainage tube (5), the mandrin (13) and the auxiliary tube (9), with a screw connection of the walls of the drainage tube and the auxiliary tube tip. The mandrin (4) in this case has no thread. The mandrin (4) has a narrowed tip range with an angular profile or projection (19) which engages a correspondingly formed internal lumen or recess (20).

What is claimed is:

1. A drainage tube arrangement for the drainage of body cavities, which arrangement comprises (1) a drainage tube which has a distal end provided with a rounded tip, a proximal end, and a central lumen through which a mandrin is slidably received, which drainage tube is made of an elastic plastic material and has at least at one of its two ends an inherent curvature, (2) a mandrin which has a distal end and a proximal end, and (3) an auxiliary tube containing a distal end and a proximal end, wherein the drainage tube is provided for its introduction into the body cavity with the mandrin for overcoming the inherent curvature of the drainage tube and thus straightening the drainage tube during said introduction, wherein the auxiliary tube is designed to be slid over the proximal end of said mandrin, and wherein a screw or recess and projection connection is provided between the drainage tube and the mandrin so as to enable the surgeon to pull the drainage tube back, as well as to rotate it, in the introduction process.

2. An arrangement as claimed in claim 1, wherein the mandrin is provided with a male thread which engages a corresponding female thread provided on the inside of the drainage tube in firm connection with said tube.

3. An arrangement as claimed in claim 2, wherein said female thread is provided on the inside of a separate sleeve element which is firmly mounted on the lumen of said drainage tube.

4. An arrangement as claimed in claim 2, wherein said female thread is provided in the lumen of said drainage tube integrally with said drainage tube.

5. An arrangement as claimed in claim 2, wherein said threads are provided on said mandrin and said drainage tube in a range adjacent to the distal ends of said mandrin and said drainage tube.

6. An arrangement as claimed in claim 2, wherein said female thread is provided in a range adjacent the proximal end of the drainage tube, and said male thread is provided in a range of said mandrin corresponding to said proximal end of the drainage tube.

7. An arrangement as claimed in claim 2, wherein the mandrin at its proximal end has a handpiece for manipulating said mandrin.

8. An arrangement as claimed in claim 2, where the distal end of said auxiliary tube has projections which engage corresponding recesses in the proximal end of said drainage tube.

9. An arrangement as claimed in claim 8, wherein said projections and said recesses are of rectangular configuration.

10. An arrangement as claimed in claim 8, wherein said projections at the distal end of said auxiliary tube extend at an angle to the axis of said tube, and
    wherein said recesses at the proximal end of said drainage tube extend at a corresponding angle to the axis of the drainage tube so as to be engaged by said projections.

11. The arrangement as claimed in claim 10, wherein the mandrin at its distal end has a section with an angular profile, and
    wherein the tip of the drainage tube has a correspondingly formed lumen into which said section of the mandrin extends.

* * * * *